United States Patent [19]

Ron

[11] Patent Number: 5,933,210
[45] Date of Patent: Aug. 3, 1999

[54] OPHTHALMOLOGICAL METHOD AND INSTRUMENT FOR PRODUCING DICHOPTIC STIMULI

[76] Inventor: Samuel Ron, 2A, Nahal Besor, Ramat, Israel, 47204

[21] Appl. No.: 08/860,924

[22] PCT Filed: Mar. 6, 1995

[86] PCT No.: PCT/US95/02757

§ 371 Date: Jul. 17, 1997

§ 102(e) Date: Jul. 17, 1997

[87] PCT Pub. No.: WO96/27324

PCT Pub. Date: Sep. 12, 1996

[51] Int. Cl.⁶ .................................................. A61B 3/00
[52] U.S. Cl. ............................................. 351/246; 351/243
[58] Field of Search .................................. 351/200, 201, 351/222, 223, 232, 233, 237, 239, 240, 243, 246; 348/51, 54; 349/15

[56] References Cited

U.S. PATENT DOCUMENTS

| 4,561,723 | 12/1985 | Hamano et al. | 349/15 |
| 5,233,458 | 8/1993 | Moffitt et al. | 351/201 |

FOREIGN PATENT DOCUMENTS

WO 91/00050  1/1991  WIPO .

OTHER PUBLICATIONS

W. Jaschinski–Kruza; "Stimulus Distance on Measurements of Dark Convergence"; Ophthalmic and Physiological Optics, vol. 10; pp. 243–251; Jul. 1990.

D. Alfred Owens; "The Resting State of the Eyes"; American Scientist, vol. 72; pp. 378–387.

W. Jaschinski–Kruza; "Eyestrain in VDT Users: Viewing Distance and Resting Position of Ocular Muscles"; pp. 69–83; 1991.

*Primary Examiner*—Huy Mai
*Attorney, Agent, or Firm*—Browdy and Neimark

[57] ABSTRACT

A method for presenting two simultaneous images having respective cross-sectional areas $A_1$ and $A_2$, on respective first and second 2-dimensional image arrays so as to be seen by an observer as a dichoptic stimulus of substantially equal intensity, involves the steps of generating a first one of the images at a predetermined first intensity on the first image array so as be perceived by a first eye of the observer only, and generating a second one of the images at a predetermined second intensity equal the first intensity multiplied by $$\frac{lgA_2}{lgA_1}$$

on the first image array so as to be perceived by a second eye of the observer only. An apparatus for carrying out the method includes a pair of LCD image arrays and a pair of spectacles having prismatic elements for allowing objects to be viewed in a desired direction only.

29 Claims, 10 Drawing Sheets

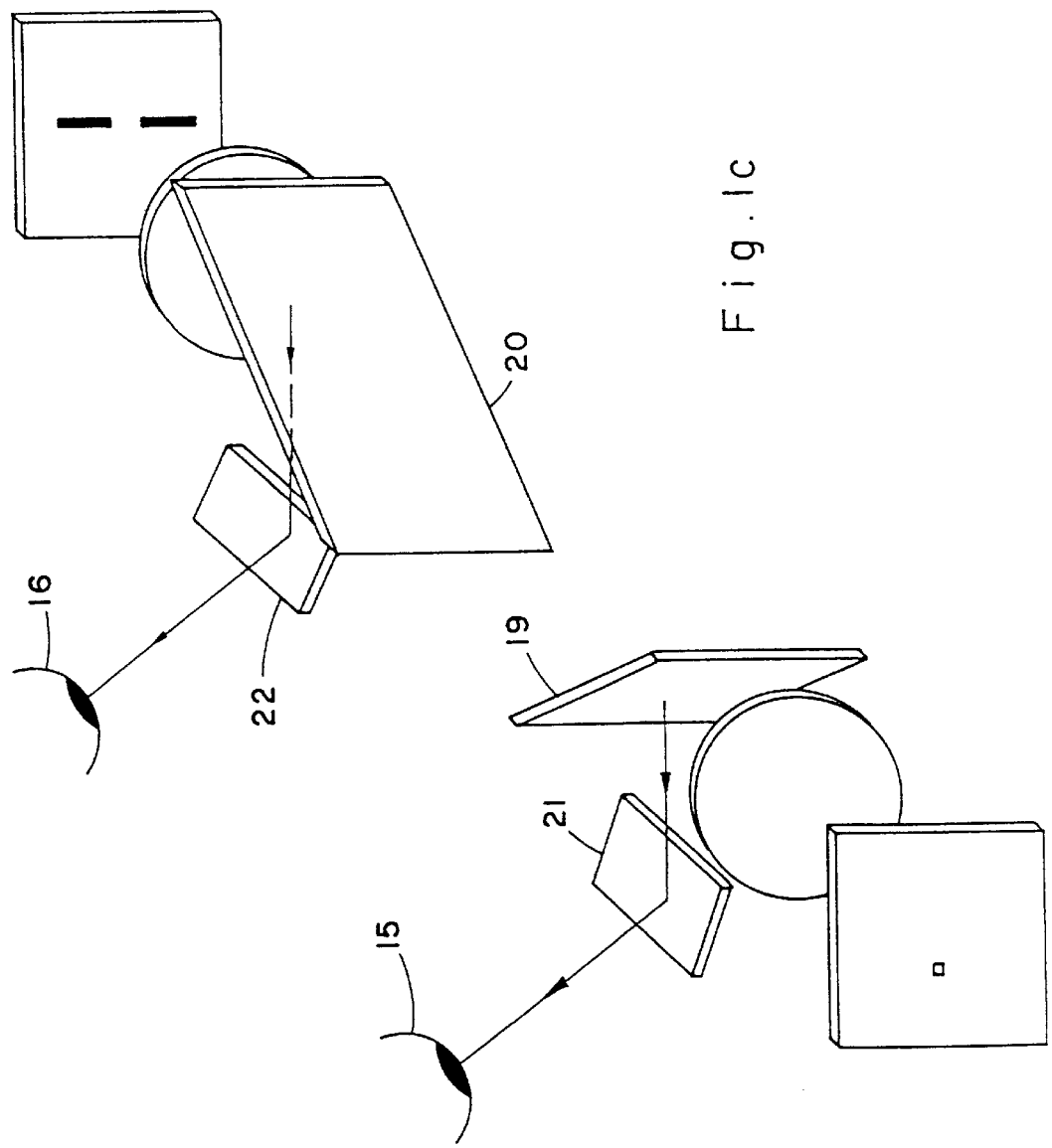

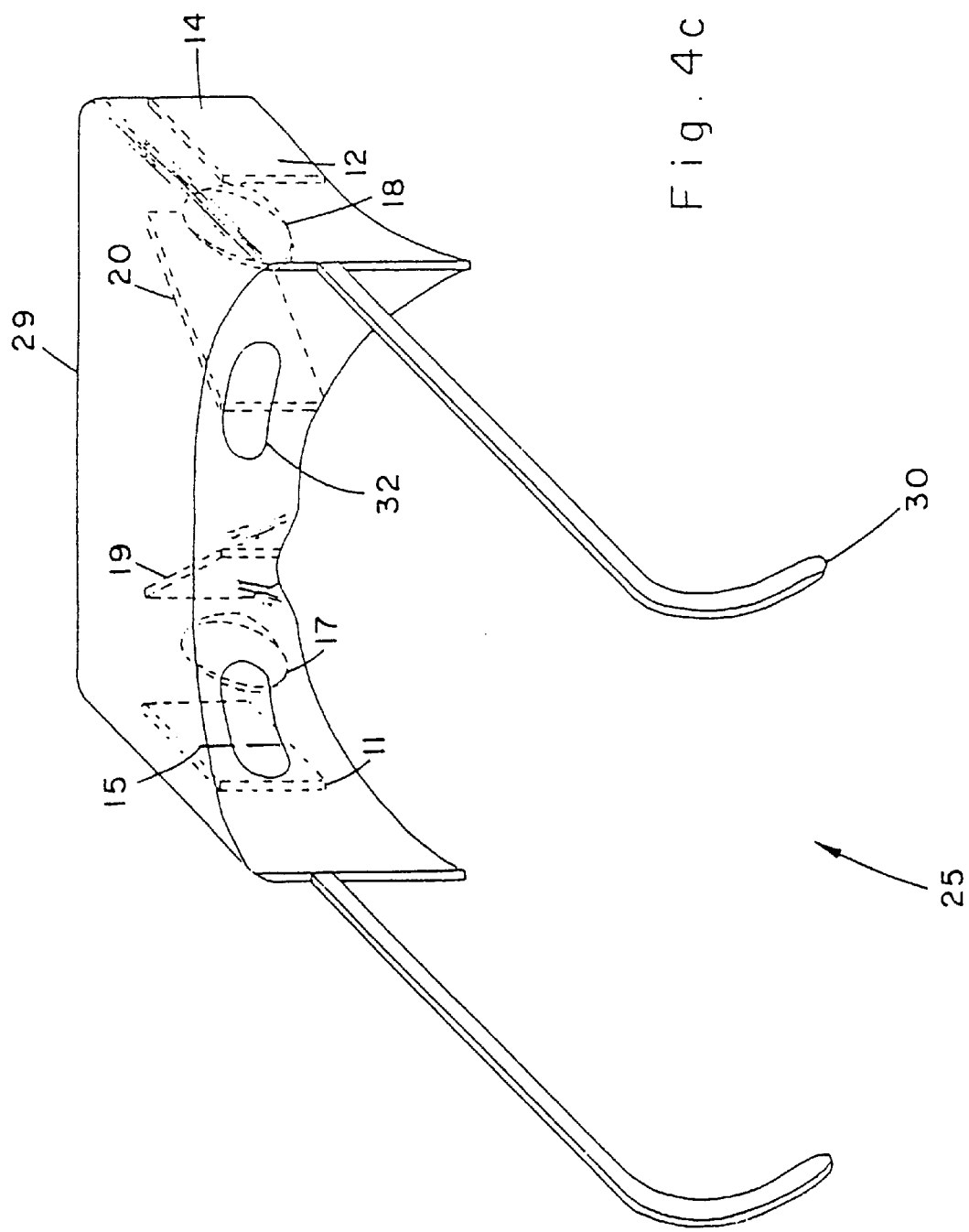

OPHTHALMOLOGICAL METHOD AND INSTRUMENT FOR PRODUCING DICHOPTIC STIMULI

FIELD OF THE INVENTION

This invention relates to a method and apparatus for presenting dichoptic stimuli, particularly for the determination of dark vergence of an observer.

BACKGROUND OF THE INVENTION

U.S. patent application Ser. No. 034,717 filed on Mar. 22, 1993 by the present Applicant and entitled "Ophthalmological Instrument For Producing Dichoptic Stimuli On A Visual Display Terminal" describes a method and system for presenting two successive images on a video display unit as a dichoptic stimulus of substantially equal intensity. A first image is displayed at a predetermined intensity so as to be seen by a first eye of an observer only, an optical shutter being used to prevent the displayed image from reaching the second eye of the observer. The first image is then extinguished and the state of the optical shutter reversed so that the first eye can no longer see the video display unit, whilst a second image is presented to the second eye. In order to prevent the second eye from seeing an after image of the first image, a neutral density filter is disposed within the light path, and the second image is illuminated at a correspondingly higher intensity so as to compensate for the attenuation factor of the neutral density filter.

Such a method may be employed to measure the dark vergence of the observer which has been found to be a major factor in determining fatigue of computer operators, in order that corrective action may be taken so that the angle subtended by an image on the computer screen at the eyes of the observer may be adjusted to the angle of dark vergence. Such corrective action may be provided by individually tailored prismatic spectacles.

U.S. application Ser. No. 034,717 thus addresses the specific need of computer operators and permits the dark vergence of such operators to be determined when looking in a substantially straight-ahead position towards a computer screen. Since images are presented on computer screens and the like as a raster scan, there is at any time only a single pixel which is illuminated, the effect of a complete image being obtained owing to the eye's persistence of vision. Further, since both the left and right eye images are presented on the same screen, any effect of after image must be suppressed so that each eye will see only its own image as a dichoptic stimulus.

Prior art relating to determination of dark vergence is fully described in the above-referenced U.S. application, the complete contents of which are incorporated herein by reference.

The above-referenced U.S. application and the prior art references discussed therein are, as indicated above, principally directed to the determination of dark vergence in a straight-ahead direction. This is fine for computer operators who do indeed work with their gaze directed substantially straight ahead. However, most text is, in fact, read with the eyes directed not straight ahead but inclined downwards. Fixating at text whilst looking down requires the cooperation of all twelve extraocular muscles attached to both eyes (i.e. medial rectus, lateral rectus, superior and inferior recti and superior and inferior oblique recti).

The prior art does not define the dark vergence when the eyes are not directed straight ahead in the horizontal direction. However, it may be expected that in any plane formed by the visual axis of the two eyes, a different dark vergence exists. Specifically, when looking down at an angle commensurate with reading, the dark vergence will be different to that associated with straight-ahead vision. To converge on text whilst looking down requires that some of the extraocular muscles contract and are thus under tension. This tension, when applied for several hours, can produce visual strain similar to the strain which results when an observer is looking at a visual display unit such as a computer screen.

From the above-referenced U.S. patent application three considerations are apparent: first, dark vergence varies between limits from one subject to another; secondly, dark vergence depends on the plane formed by the visual axis of the two eyes; and thirdly, the optimal distance between an operator and a visual display unit or between someone who is reading text and the text material itself depends on the subject's dark focus.

In the above-referenced U.S. patent application, a method is described in which the dichoptic stimuli to the eyes is presented so as to force each eye to see only its image. One of the images is a pair of nonious bars having a central gap and the other image is a movable dot which can be aligned by the observer with the gap in the nonious bars. When the two images are perceived as aligned by the observer, any actual displacement between the images is measured and this, together with the interpupillary distance of the observer, permits determination of the observer's dark vergence, in accordance with the following formula:

$$D_c = \frac{P_d D_o}{P_d - f(T)}$$

where:
  $DC_c$ is the distance of dark vergence;
  $P_d$ is the interpupillary distance;
  $D_o$ is the distance of the optical pathway from the observer to a viewing plane of the video display unit; and
  $f(T)$ is a polynomial function of the measured displacement T between the two dichoptic images which approximates the measured displacement T for at least a latter portion of said sequence of images.

Although the method and apparatus disclosed in the above-referenced U.S. application is well-suited for the determination of dark vergence of computer operators, it requires a computer which must be enclosed within an optical tunnel as shown in FIG. 5 of the U.S. application, and the resulting apparatus is therefore bulky and relatively expensive. It would clearly be desirable to extend the method disclosed in the above-referenced U.S. application so as to allow for the determination of dark vergence in directions other than straight ahead and, further, to permit such determination with a much more compact apparatus not requiring a computer. Such a simplified apparatus should clearly be within the budget of optometrists so as to allow for the determination of a patient's dark vergence as a completely standard procedure together with conventional eye tests. Then, when appropriate, special prismatic lenses may be prescribed, together with, if necessary, conventional refracting elements, in order to allow for the correction of dark vergence. Such correction is described per se in the above-referenced U.S. patent application.

It is also known that there are well known methods and systems for recording eye position or line-of-sight in the dark, some of which will now briefly be reviewed.

It is well known that there is a corneoretinal potential originating in the retinal pigment epithelium. This potential can be registered indirectly with skin electrodes placed in the horizonal plane close to the eyes' edge and, if necessary, in the vertical direction by placing one electrode above the upper eyelid and another electrode just below the lower eyelid. This method, called electro-oculography (EOG), measures the relative value of the corneofundal potential and the voltage between the electrodes which correlates with the position of the eye, separately in the horizontal and the vertical directions. Based on the measured potentials, the spatial location of the line-of-sight of each eye can be determined.

Also known is the double Purkinje eye tracker which uses the corneal reflex or first Purkinje image to determine eye position. According to this technique, a light is shined on to the eye and approximately 2.5% of the incident light is reflected from the surface of the eye to a photocell. When the eyes rotate, the reflected light changes its angle relative to the rotated eyes and the voltage generated by the photocell varies in known sinusoidal manner so that by measuring the voltage, the rotation of the eye can be determined.

Eye position can also be determined as a function of the position of the iris-sclera boundary (the limbus) with respect to the head. The ratio between the dark iris and the bright sclera observed on the left and right side of the eye may be measured directly with respective photo sensors responding to infrared light projected on to each of the eyes. This ratio is directly related to the position of the eyes in the plane formed by the two photo sensors.

Thus, in one example, respective left and right sensors are placed at eye level so as to provide a signal proportional to the eye position in the horizontal plane, whilst up and down sensors are placed above the eyebrow and below the eyelid so as to provide a signal proportional to the eye position in the vertical plane. Alternatively, eye position can be measured indirectly by projecting the image of the eye (e.g. by means of a television camera) and computing the position of the eye from this image.

It has also been proposed to image the eye with a small infrared charge-coupled device (CCD) image sensor coupled to a video tape recorder. The resulting image may be fed to a computer for analysis so as to determine the horizontal and vertical components of the eye position.

All of these methods are suitable only for determination of the eyes' orientation or position, none having any direct relevance or application to the determination of a subject's dark vergence. This having been said, the dark vergence could be determined by measuring the eyes' orientation when the subject is completely dark-adapted. However, in order to do this, it would first be necessary to dark-adapt the subject. It is not possible to employ any of the known methods for determining the eyes' orientation for determining dark vergence because, when the eyes come to rest in the dark, in the absence of any visual stimulus the eyes float so that their "line-of-sight" is essentially arbitrary. In order to employ existing techniques for measuring the eyes' orientation so as to determine therefrom a subject's dark vergence, it would first be necessary to eliminate the problem of floatation of the eyes so as to ensure that the eyes become directed along a desired line-of-sight. No prior art solution to this problem has been proposed.

SUMMARY OF THE INVENTION

It is a principal object of the invention to provide a method and apparatus for presenting dichoptic stimuli on a pair of two-dimensional image arrays.

It is a further object of the invention to provide a method and apparatus for determining the dark vergence of a subject when looking down at text material.

It is a further object of the invention to provide a method and apparatus which may be employed in conjunction with any existing system for measuring eye position so as to determine from such measurement a subject's dark vergence.

Yet another object of the invention is to present the dichoptic stimuli at a predetermined level above the subject's individual visual threshold.

A still further object of the invention is to provide correction spectacles for correcting a subject's dark vergence so as to reduce the subject's visual fatigue.

According to a broad aspect of the invention there is provided a method for presenting two simultaneous images having respective cross-sectional areas $A_1$ and $A_2$, on respective first and second, 2-dimensional image arrays so as to be seen by an observer as a dichoptic stimulus of substantially equal intensity, the method comprising the steps of:

(a) generating a first one of the images at a predetermined first intensity, on the first image array so as be perceived by a first eye of the observer only, (b) generating a second one of the images at a predetermined second intensity equal the first intensity multiplied by $$\frac{lgA_2}{lgA_1}$$

on the first image array so as be perceived by a second eye of the observer only.

BRIEF DESCRIPTION OF THE DRAWINGS

In order to understand the invention and to see how the same may be carried out in practice, some preferred embodiments will now be described, by way of non-limiting example only, with reference to the accompanying drawings, in which:

FIGS. 1a, 1b and 1c are optical diagrams showing schematically an apparatus according to the invention for presenting dichoptic stimuli on LCD image arrays;

FIGS. 4a, 4b and 4c show schematically a pair of spectacles for holding therein the optical arrangement shown in FIG. 1a;

FIG. 8 is a block diagram showing functionally a controller for use with the apparatus depicted in FIG. 1a.

DETAILED DESCRIPTION OF PREFERRED EMBODIMENTS

Figure 1A:
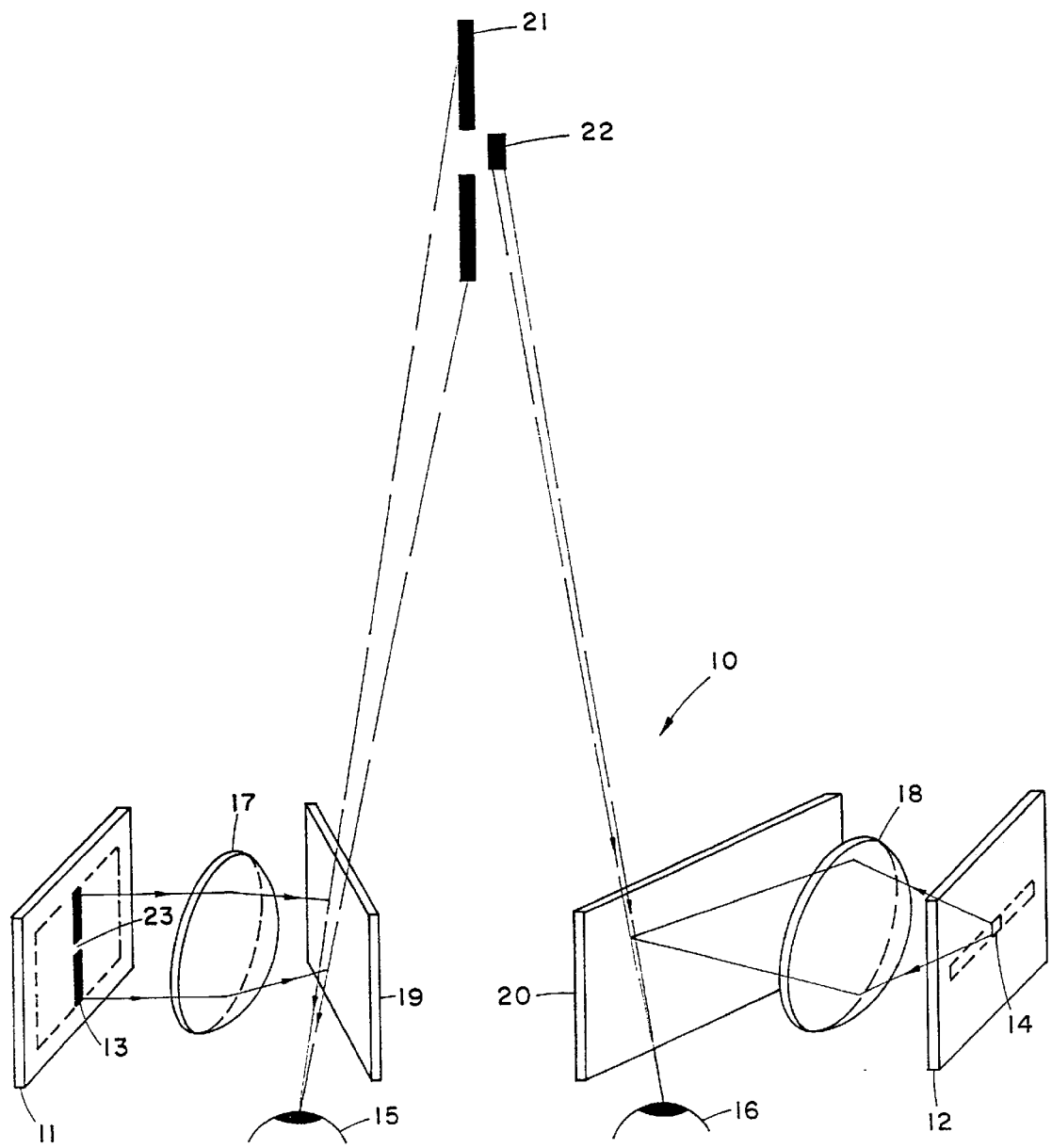

FIG. 1a shows pictorially an apparatus depicted generally as 10 for determining an observer's dark vergence. A pair of LCDs 11 and 12 constituting, respectively, first and second two-dimensional image arrays, display, respectively, a pair of nonious bars 13 and a dot 14. The nonious bars 13 and the dot 14 can be moved simultaneously in mutually opposite directions by means of a control box (shown in FIG. 8) so as bring the two images respectively closer together or further apart, as required. The control box allows an observer to move the nonious bars 13 and the dot 14 so as to bring the dot 14 into apparent alignment with a gap 23 in the nonious bars 13.

The images 13 and 14 are displayed on the respective LCDs 11 and 12 simultaneously for viewing by respective eyes 15 and 16 of an observer, thus avoiding any of the problems associated with Applicant's previous solution based on a VDU display wherein care had to be taken to the left and right eye images from being seen by the opposite eyes.

The apparatus 10 further includes a pair of converging lenses 17 and 18 for directing respective images 13 and 14 on to respective mirrors 19 and 20 which are so inclined as to produce virtual images 21 and 22, respectively, of the two images 13 and 14. By moving the image 13 of the nonious bars to the left or right and the image 14 of the dot in the opposite direction, the virtual image 21 of the nonious bars 13 and the virtual image 22 of the dot 14 may be brought into apparent alignment.

Figure 1B:
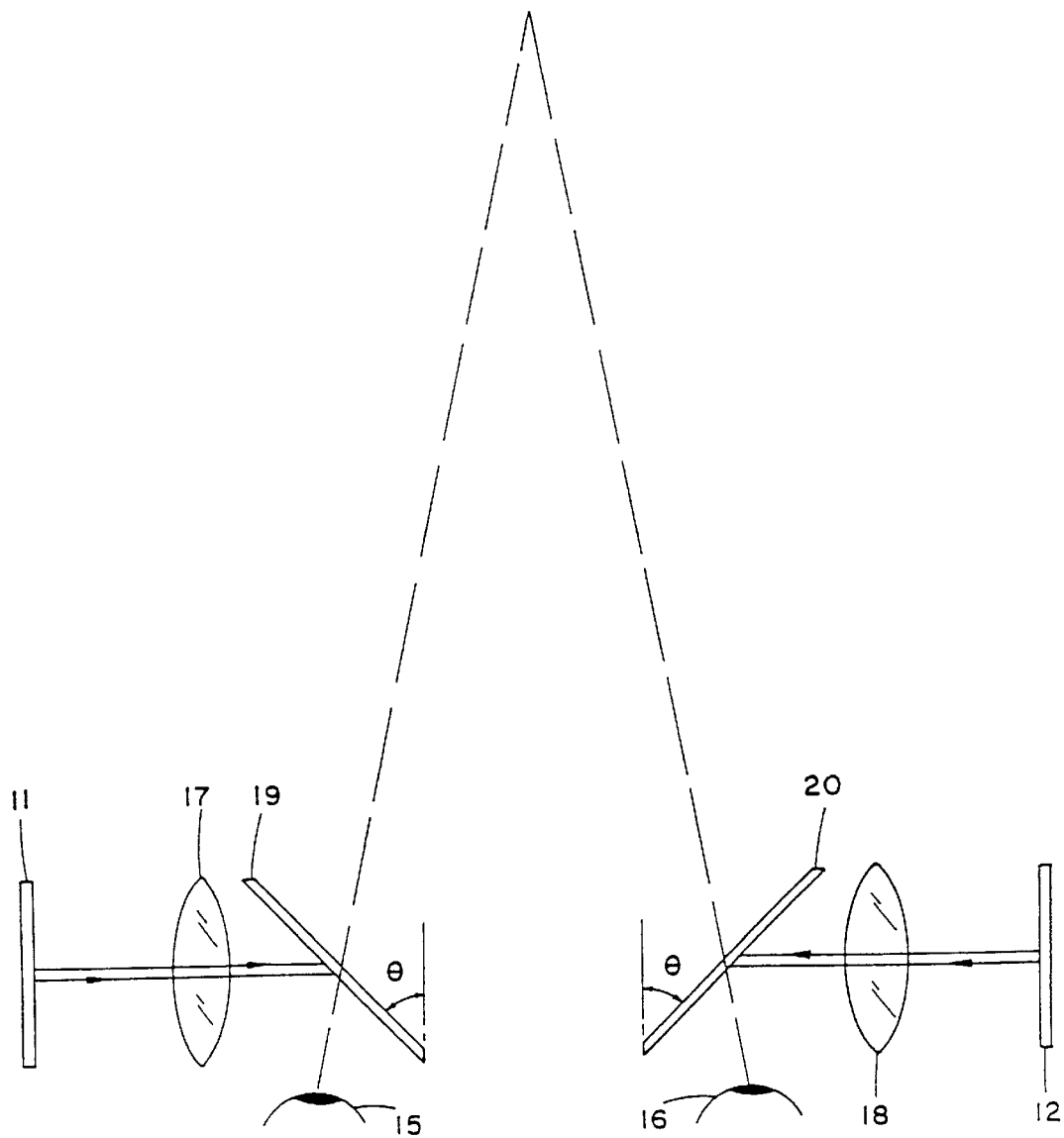

FIG. 1b is a plan view of the apparatus shown in FIG. 1a. The angle θ of the inclined mirrors is preadjusted such that for an average interpupillary distance of 66 mm, the perceived stimulus will be at a distance of 2 feet (66 cm). The previously measured interpupillary distance also determines the distance between the mirrors 19 and 20. The two sides of the optical arrangement comprising the respective LCDs, lenses and mirrors may be moved closer together or further apart so as to align the respective images symmetrically with the two eyes 15 and 16 of the observer.

FIG. 1c shows pictorially a modification to the apparatus 10 described above with reference to FIG. 1a, so as to allow for the determination of dark vergence when an observer is looking down at text material, for example, placed on a table in front of the observer. Obstructions (not shown) are placed in the optical paths shown in FIG. 1a so as to prevent the observer's eyes 15 and 16 from seeing the respective images 13 and 14 when looking straight ahead. Instead, reflecting mirrors 21 and 22 are placed in the respective optical paths so as to intercept the images reflected by the mirrors 19 and 20 and reflect them upwards towards the respective eyes 15 and 16 of the observer. By such means, the observer can only see the virtual images 21 and 22 when looking, down into the mirrors 19 and 20 and the resulting calculation of dark vergence is thus matched to downward-directed viewing instead of straight-ahead viewing.

Figure 2:
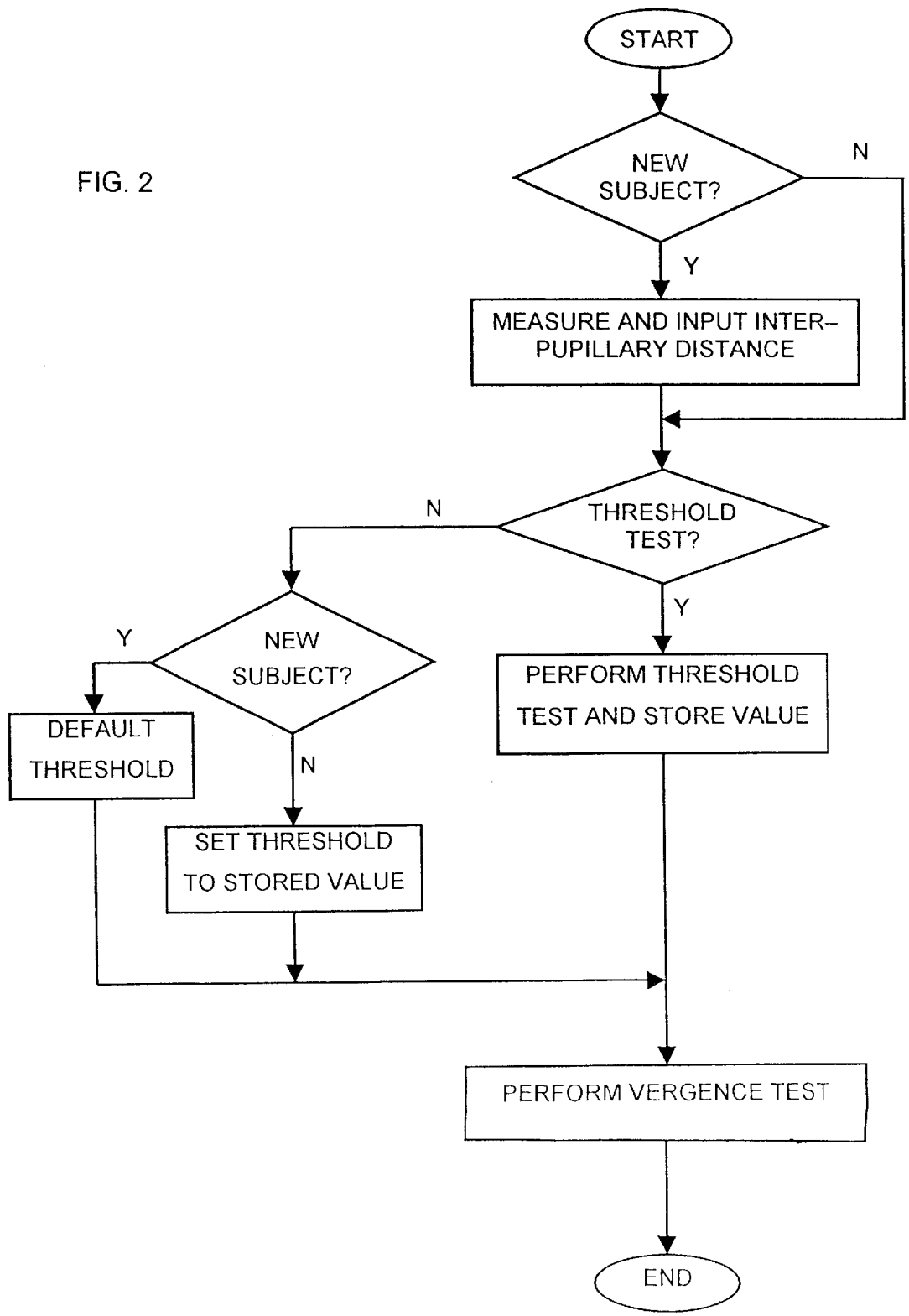
FIG. 2 is a flow diagram showing the principal operating steps for determining, an observer's dark vergence or his visual threshold.

FIG. 2 shows the principal operating steps in a method to be used with the apparatus 10 described above with reference to FIGS. 1a to 1c of the drawings. Initially, the subject's visual threshold is determined by presenting on the LCDs successive pairs of bars and dots, the test being terminated after forty sequences or beforehand, as described by Lieberman, H. R. and Pentland, A. P. in *"Microcomputer-based estimation of psychophysical thresholds: The Best PEST"* in Behavior Research Methods & Instrumentation 1982, Vol. 14(1), 21–25 incorporated herein by reference.

Because the size of the dot 14 is much smaller than that of the bars 13, the luminosity of the dot 14 must be increased so that both images will appear to the eye at the same intensity. Owing to the logarithmic relationship between luminosity and eye response, the luminosity of the dot 14 must be increased by a factor equal to the ratio of the logarithms of the cross-sectional areas of the bars 13 to the dot 14. In practice, the cross-sectional areas of the respective images are proportional to the number of pixels contained therein and thus the required equalizing factor is simply equal to the ratio of the logarithms of the respective numbers of pixels in the two images. Once the threshold has been determined for the individual subject under test, subsequent stimuli are presented at an intensity equal to the visual threshold intensity multiplied by a factor greater than 1 such that the stimuli can be seen comfortably without overloading the visual system. In practice, the required factor should be between 1.5 and 1.9. Displaying images at an intensity less than 1.5 results in an increased probability that the stimuli will not be seen by the observer whilst multiplying the display intensity by a factor greater than 1.9 is likely to overload the eyes' visual system.

Having, determined the visual threshold for the observer, the dark vergence is determined by presenting successive sequences of images on the LCDs, the observer in each case moving the dot image 14 to the left or right, as required, in order to bring the dot image 14 into alignment with the gap 23 between the nonious bars 13. The tests stop after 40 sequences of stimuli have been presented or when the observer indicates that the respective images are in apparent alignment within a preset error margin. Any actual displacement between the two images is then measured for the final five consecutive sequences and averaged, whereupon the dark vergence may be calculated in accordance with the formula:

$$D_c = \frac{P_d D_o}{P_d - f(T)}$$

where:

$D_c$ is the distance of dark vergence;

$P_d$ is the interpupillary distance;

$D_o$ is the distance of the optical pathway from the observer to a viewing plane of the video display unit; and $f(T)$ is a polynomial function of the measured displacement T between the two dichoptic images which approximates the measured displacement T for at least a latter portion of said sequence of images.

Thus, as shown in FIG. 2, at the start of the test for a new subject, the interpupillary distance, having previously been measured, is entered. Thereafter, the option is given to perform either the threshold test or the vergence test. When the threshold test is performed, the stimuli appear to the subject as previously explained and the subject responds by pressing a button so as to indicate whether or not he has seen the target.

Thereafter the vergence test is performed. As shown in FIG. 2, when the vergence test is performed without the subject's visual threshold having been first determined, the stimulus intensity for a new subject is provided by a default setting. Alternatively, when a test is repeated for the same subject, the previously stored threshold value is used. When the vergence test is performed, up to 40 sequences of dichoptic stimuli are presented until the PEST results reach a confidence limit of 95%, whereupon the test terminates. A short melody signifies completion of the test.

Figure 3:
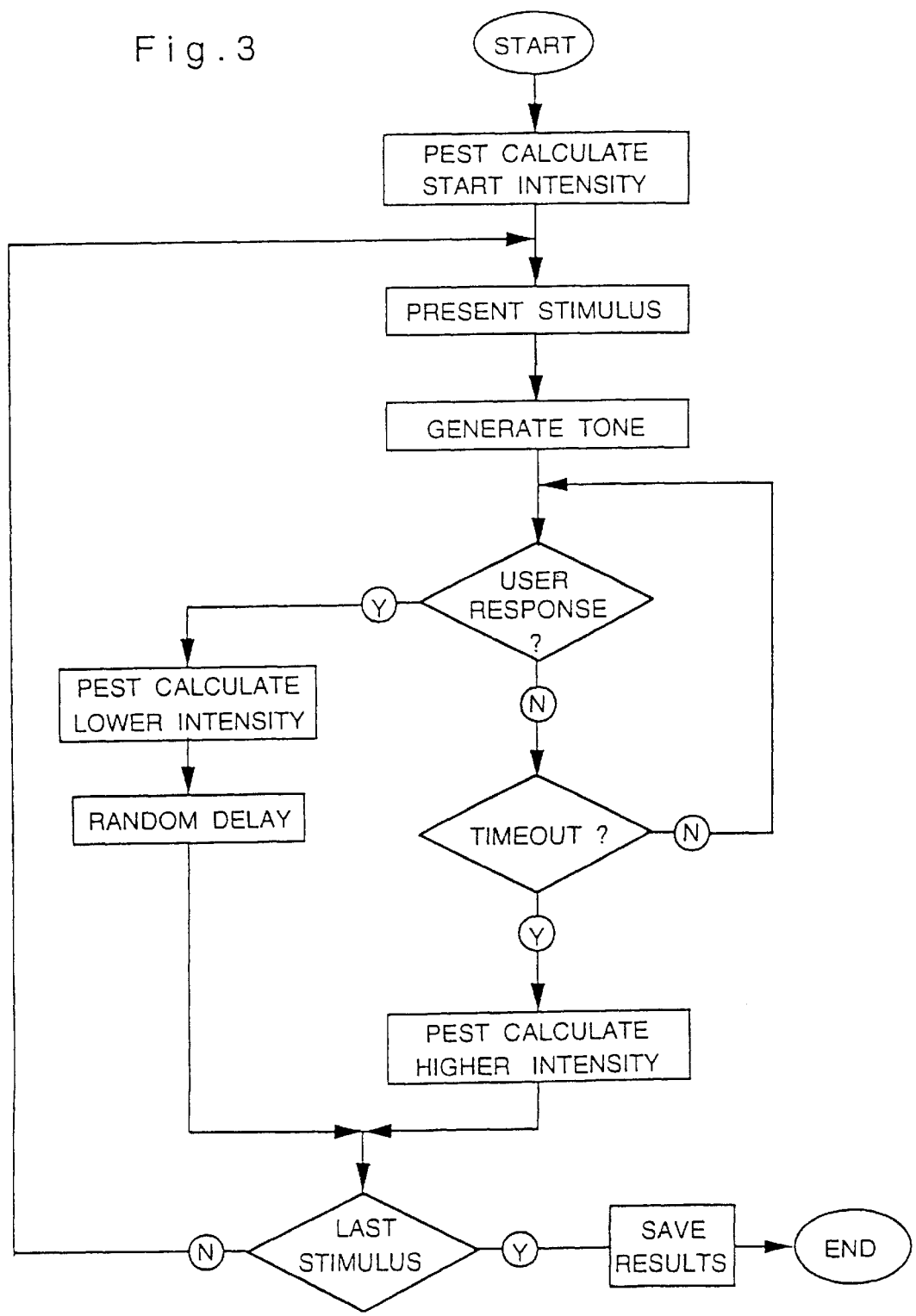
FIG. 3 is a flow diagram showing the principal operating steps for determining an observer's visual threshold.

FIG. 3 shows in more detail the principal steps associated with the threshold test. The PEST calculates the start intensity at which the first stimulus is presented, whereupon a tone is generated so as to prompt the subject that a stimulus has been displayed. The subject is then given 4 seconds in which to confirm that the stimulus is visible, upon confirmation of which the PEST calculates a new, lower intensity and, after a random delay T a new stimulus is presented having the calculated, lower intensity. Otherwise, if after a timeout of 4 seconds the subject has not confirmed that the stimulus was visible, then the PEST calculates a new higher intensity and a new stimulus, having this higher intensity, is then presented. The whole cycle repeats until the PEST algorithm indicates that the intensity at which stimuli are presented corresponds to the visual threshold intensity of the subject. The visual threshold is then stored and the threshold test terminates.

The threshold test terminates when five consecutive measurements converge within a preset error margin to the visual threshold, this being signified to the subject by means of a short melody. The threshold value is then multiplied by a fixed constant between 1.5 and 1.9 so as to provide a base threshold for performing the vergence test.

The random delay T is derived by measuring a reaction time $T_1$ between displaying a first stimulus and the observer indicating an apparent misalignment, whereupon the time delay T is determined as a quasi-random function larger than and independent of the reaction time $T_1$ of the observer between specified lower and upper limits.

It should he noted that the threshold test may be performed according to different logic. Thus, according to the logic shown in FIG. 3 the assumption is that failure to respond on the part of the subject indicates that he did not see the stimulus, in which case PEST calculates a new, higher intensity. However, failure to respond may simply be due to confusion on the part of the subject, and the threshold test may be adapted to display the next stimulus at the same intensity and prompt the user again for a response. As more stimuli are presented throughout the course of the test, the stimulus intensity converges to, and hunts around, the subject's visual threshold intensity. When this happens, PEST will decrease or increase the stimulus intensity according to whether the previous stimulus were visible or not to the subject.

In practice, the visual threshold for each eye of an observer may be different. Thus, if the visual threshold test is performed for both of a subject's eyes together, then the "strong" eye will see an image even when the intensity thereof is too low for the "weak" eye to perceive it. Since, when the vergence test is performed, the dichoptic stimuli are presented as separate images for each eye, ideally the dichoptic stimuli should be presented at a fixed intensity relative to the corresponding threshold intensity of the respective eye. This, of course, requires that the visual threshold intensity be determined for each of a subject's eyes separately. This may be done quite simply by placing an obstruction in front of one eye and performing the threshold test for the unobstructed eye and then repeating the process for the other eye.

Figure 4A:
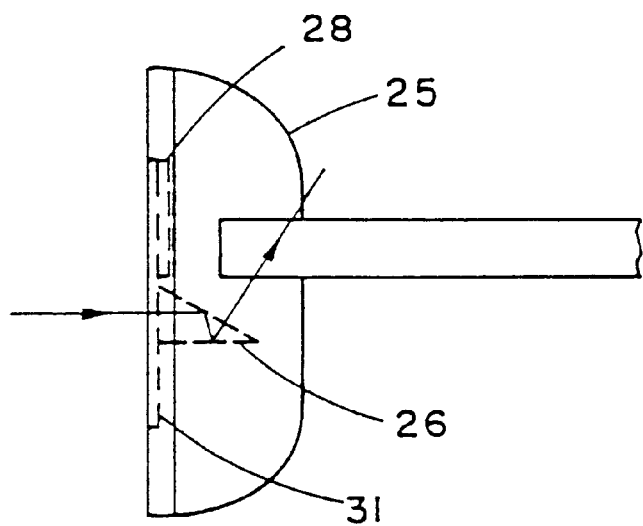
Figure 4B:
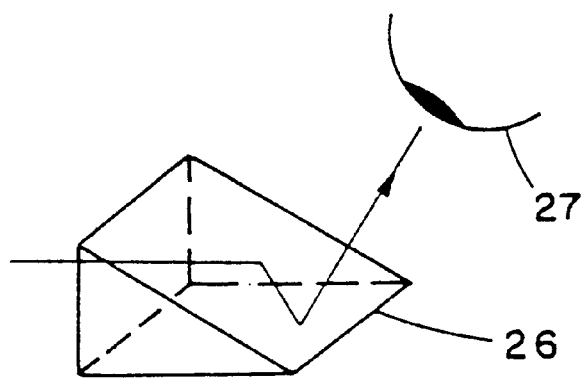

Referring now to FIGS. 4a, 4b and 4c there are shown schematically a pair of spectacles depicted generally as 25 including therein one of the optical arrangements shown schematically in FIGS. 1a to 1c of the drawings. The spectacles 25 also contain a prismatic element 26 for allowing light from a straight-ahead target to reach the observer's eye 27 only when the observer is looking down. This arrangement corresponds to the optical system described above with reference to FIG. 1c of the drawings. In order to prevent straight-ahead vision, an obstruction 28 is placed in the optical path and is fixed within a frame 29 of the spectacles to which corresponding support arms 30 are connected as shown in FIG. 4c.

The spectacles 25 shown in FIG. 4c may also be adapted for use with a VDU wherein dichoptic stimuli are presented as successive images. Since it is important that each eye sees only its own image, it is necessary in this case to provide a shutter 31 in each side of the spectacle frame 29 and which is synchronized to the VDU images as explained in Applicant's previous U.S. application Ser. No. 034,717. The spectacles 25 are also provided with a pair of openings 32 for allowing the respective eyes of the observer to see the virtual images of the dot 14 and the nonious bars 15.

Figure 5:
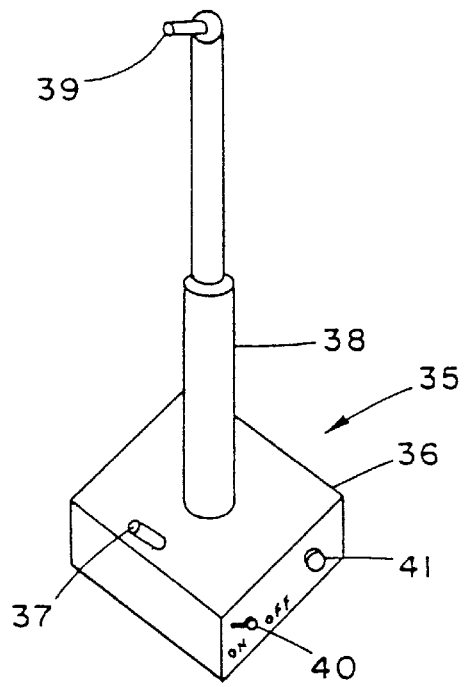
FIG. 5 is a pictorial representation of a device for producing a visual stimulus at different heights relative to an observer's eyes.

FIG. 5 shows a device 35 for emitting visual stimuli at a desired height when an observer is dark-adapted, so as to direct his gaze in a required direction. The device 35 comprises a base 36 mounted on which is a first LED light source 37 and a telescopic arm 38 at the top of which is mounted a second LED light source 39. One only of the LEDs 37 and 39 is activated by means of a selector switch 40 so as to produce flashes every 2–5 sec. and each having a duration of less than 100 ms. The intensity of the flashes may itself be adjusted by means of an adjustment means 41.

Figure 6:
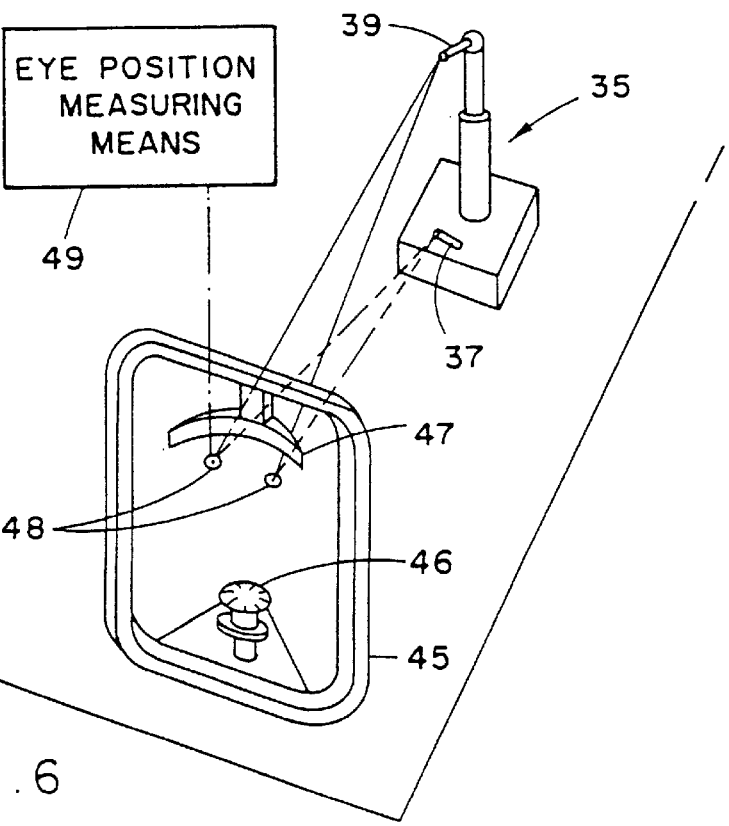
FIGS. 6 show schematically an apparatus for determining an observer's dark vergence using the device shown in FIG. 5.

FIG. 6 shows pictorially the principal components of an apparatus for utilizing the device 35 shown in FIG. 5 together with any standard system for determining eye position, in order to determine an observer's dark vergence $\theta_c$. The observer's head (not shown) is clamped within a frame 45 so that the observer's chin is fixed on a chin rest 46 and his forehead is held against a headrest 47. The observer's eyes are shown schematically as 48 and their position may be determined by means of an eye position measuring means shown schematically as 49 and being a standard optical device such as described in the opening section of the specification and not itself being a feature of the invention.

In use, the eye position measuring means 49 is calibrated in known manner so as to permit determination of a calibration curve being a polynomial function $K = f(\theta)$ of the relationship between signal magnitude K in volts produced by the eye position measuring means 49 and eye position $\theta$ in degrees. Thereafter, in order to determine the observer's dark vergence when looking in a straight-ahead direction, the observer is first dark adapted and the LED 39 is energized so as to produce short duration flashes every 2 to 5 sec. The duration of the flashes is less than 100 ms which is too short to allow the observer's eyes 48 to converge on to the image (i.e. to focus on to the LED 39) and thus each eye sees a separate image of the LED 39 as a dichoptic stimulus. The position of the stimulus directs the observer's gaze in the required direction and the eyes' new position corresponding to the dark vergence angle $\theta_c$ in the required direction is determined by measuring the output signal voltage of the eye position measuring means 49 and deriving the dark vergence $\theta_c$ of the observer from the predetermined calibration curve. If, instead, it is desired to measure the observer's dark vergence when looking down, then the LED 37 is energized so as to direct the observer's eyes downwards and the same procedure is performed.

In either case, the visual stimulus is a sequence of 40 flashes appearing every 2 to 5 seconds and each having a duration less than 100 ms, and after each flash the mean eye position $P_i$ is measured for approximately 1 second. The dark vergence $\theta_o$ is calculated in accordance with the formula:

$$\theta_c = \frac{K}{n} \sum_{n=1}^{40} P_i.$$

Figure 7:
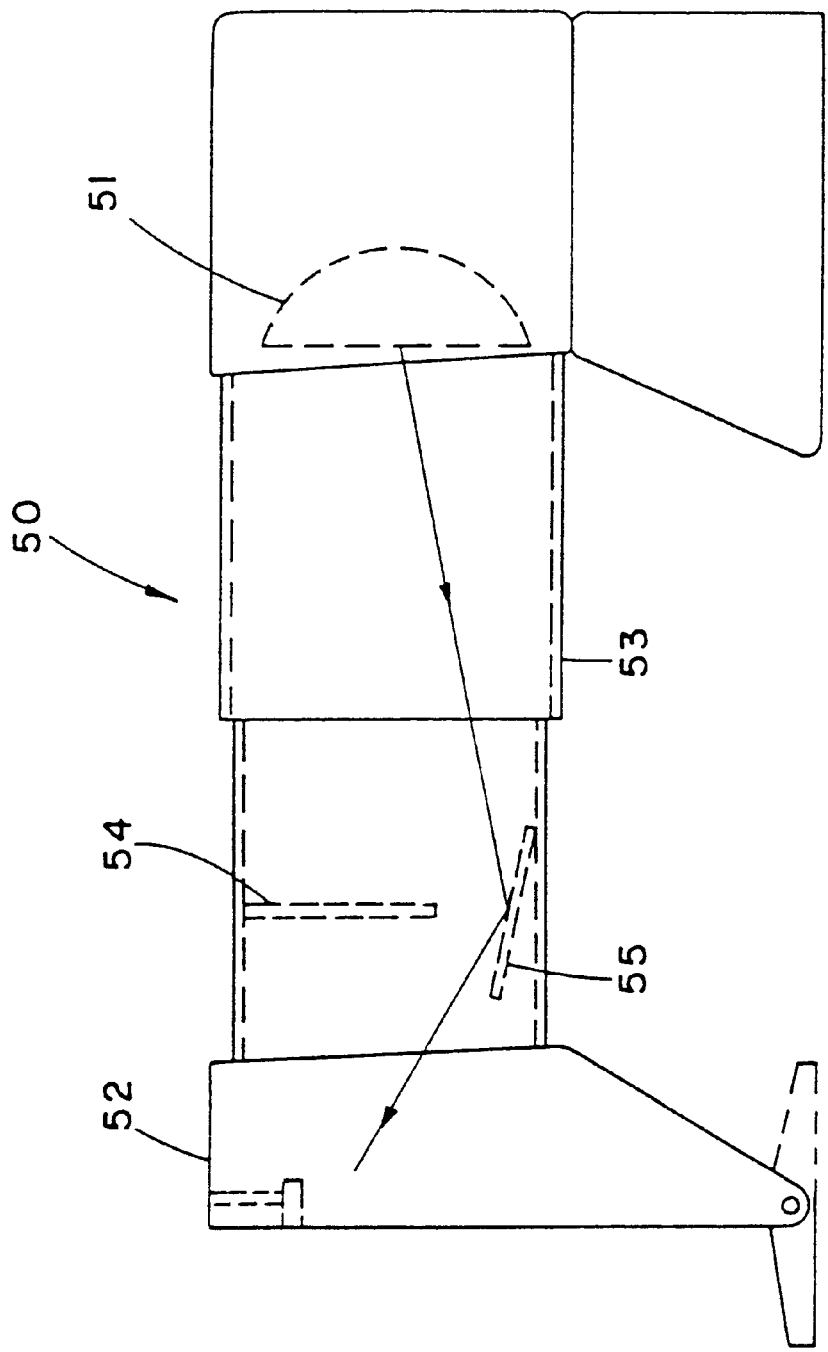
FIG. 7 shows a modification to the apparatus described in Applicant's previous U.S. application Ser. No. 034,717 for determining an observer's dark vergence other than in a straight-ahead direction.

FIG. 7 is a side elevation of an apparatus 50 comprising a VDU display 51, a hood 52 and a telescopic tunnel 53 for determining dark vergence of an observer looking at the VDU 51 in accordance with Applicant's previous U.S. application Ser. No. 034,717. The configuration described in Applicants' previous application allows for the determination of an observer's dark vergence when looking straight ahead at the VDU 51. In order to allow for the determination of dark vergence when looking down, an obstruction 54 is placed in the optical path between the VDU 51 and the hood 52 and a reflecting means 55 is mounted within the telescopic tunnel 53 for reflecting an image on the VDU 51 upwards towards the observer's eyes (not shown). Subsequent determination of the observer's dark vergence in accordance with Applicant's above-mentioned U.S. application will then relate to the observer looking down instead of straight ahead.

Figure 8:
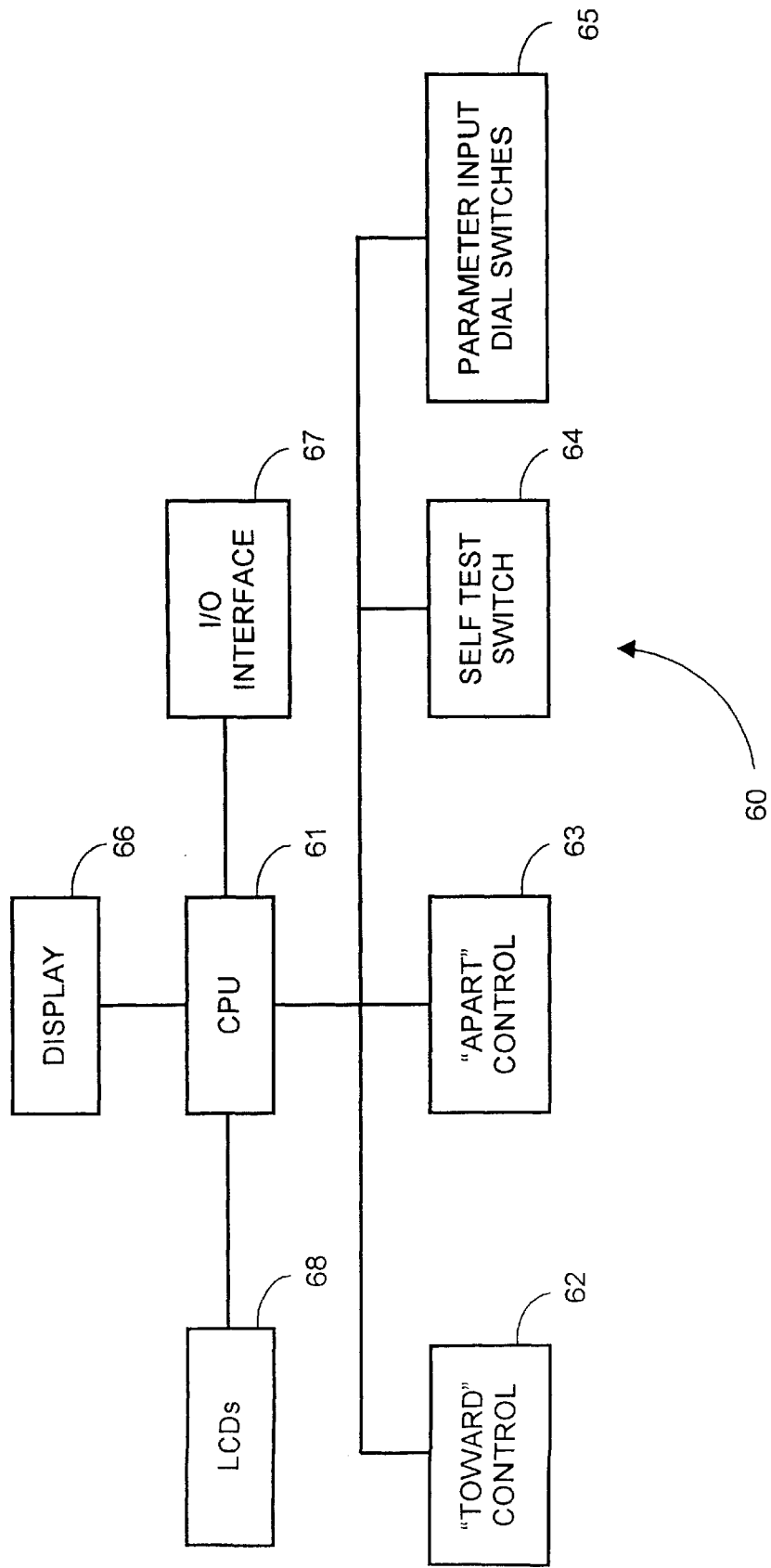

FIG. 8 is a block diagram showing the principal components in a controller 60 for use with the apparatus shown in FIG. 1a for determining an observer's dark vergence. The controller 60 comprises a CPU 61 coupled to which are "toward" and "apart" control buttons 62 and 63, a test selector switch 64 and a parameter input means 65. The parameter input means 65 comprises a pair of dial switches for respectively entering the tens and units digits of the observer's interpupillary distance. The input interpupillary distance may be seen visually on a display 66 coupled to the CPU 61. Also coupled to the CPU 61 is an I/O interface 67 for allowing, connection of the controller 60 to an external printer (not shown) by a serial or parallel interface.

The controller 60 is battery operated and is automatically energized when any of the control buttons 62 or 63 or the switches 64 and 65 are activated. Likewise, when none of the switches is activated for a period of 2 minutes, the controller 60 is automatically shut down.

The test select switch 64 allows for selection of either the threshold test or the vergence test as described above with particular reference to FIGS. 2 and 3 of the drawings.

A pair of LCDs 68 is coupled to the CPU 61 for producing respective left and right eye images: which may be moved respectively closer together or further apart by means of the respective control switches 62 and 63. The CPU 61 constitutes respective first and second control means for illuminating respective pixels in the corresponding LCDs 68 whilst the "toward" and "apart" control switches 62 and 63, together, constitute a third control means operable by the observer for indicating an apparent displacement between the two images on the respective LCDs 68, whereby the CPU 61 moves the second image in a direction to minimize the apparent misalignment.

It will be appreciated that although the invention has been described with particular reference to the use of LCDs, the general principles of the invention are equally well applicable to other types of two-dimensional image array. For example, a miniature TV monitor, a matrix of LEDs or a fiber-optic bundle may be employed instead of the LCD arrays described in the preferred embodiment. It will further be appreciated that the invention encompasses within its scope the use of a VDU terminal as described in Applicant's previous U.S. application Ser. No. 034,717 and including therein the additional components for directing an observer's gaze in a desired direction, whereby the resulting measurement of dark vergence is appropriate to the selected direction of vision.

I claim:

1. A method for presenting two simultaneous images having respective cross-sectional areas $A_1$ and $A_2$, on respective first and second 2-dimensional image arrays so as to be seen by an observer as a pair of dichoptic stimuli of substantially equal intensity, the method comprising the steps of:
   (a) generating a first one of the images at a predetermined first intensity on the first image array so as be perceived by a first eye of the observer only,
   (b) generating a second one of the images at a predetermined second intensity equal the first intensity multiplied by $$\frac{lgA_2}{lgA_1}$$

on the first image array so as be perceived by a second eye of the observer only.

2. The method according to claim 1, wherein the 2-dimensional image arrays are LCDs.

3. A method for determining a dark vergence of an observer, comprising the steps of:
   (a) measuring an interpupillary distance of the observer,
   (b) determining a visual threshold of the observer's eyes,
   (c) illuminating pixels in first and second image arrays so as to present a sequence of two simultaneous images on respective first and second 2-dimensional image arrays as a pair of dichoptic stimuli of substantially equal intensity greater than the visual threshold determined in step (b) by a predetermined equalizing factor such that the two images may be moved mutually closer together or further apart by illuminating different pixels in at least one of the first and second image arrays,
   (d) for each sequence of images presented on the image arrays, extinguishing and illuminating pixels so as to move the two images relatively closer together or further apart until both images appear to the observer to be aligned,
   (e) measuring any actual displacement T between the two images, and
   (f) calculating a distance of dark vergence according to the formula:

$$D_c = \frac{P_d D_o}{P_d - f(T)}$$

where:
   $D_c$ is the distance of dark vergence;
   $P_d$ is the interpupillary distance;
   $D_o$ is the distance of an optical pathway from the observer to a viewing plane of the image arrays; and
   f(T) is a polynomial function of the measured displacement T between the pair of dichoptic stimuli which approximates the measured displacement T for at least a predetermined number of images at an end of said sequence.

4. The method according to claim 3 for determining the observer's dark vergence in a predetermined direction, wherein prior to performing step (c) there is further included the step of preventing the observer from seeing the dichoptic stimuli other than by looking in said predetermined direction.

5. The method according to claim 4, wherein the dichoptic stimuli are propagated to the eyes of the observer via an inclined reflecting element which is normal to the eyes when they are directed in said predetermined direction, and the step of preventing includes disposing an optically dark element in front of the eyes of the observer so as to prevent straight-ahead vision.

6. The method according to claim 3, wherein for each sequence of dichoptic images the observer indicates any apparent misalignment between the two images whereby in a successive sequence of images, the two images may be moved relatively closer together or further apart so as to compensate for said apparent misalignment.

7. The method according to claim 6, wherein step (c) includes the steps of:
- (c1) displaying a first pair of images on the image arrays so as to be seen by respective eyes of the observer,
- (c2) the observer indicating an apparent misalignment between the first pair of images, and
- (c3) displaying a second pair of images at a random time delay T after the observer indicates said apparent misalignment between the first pair of images.

8. The method according to claim 7, wherein after step (c2) there is further included the step of:
- (c3') measuring a response time $T_1$ between displaying said first pair of images and the observer indicating said apparent misalignment;
- the time delay T being a quasi-random function larger than and independent of the response time $T_1$ of the observer between specified lower and upper limits.

9. The method according to claim 3, wherein each of the two images has a predetermined intensity equal to a predetermined level above the measured visual threshold of the observer.

10. The method according to claim 3, wherein each of the displayed images has a predetermined intensity equal to a predetermined level above a respective visual threshold measured in respect of a corresponding eye of the observer.

11. A method for determining a dark vergence of an observer, comprising the steps of:
- (a) measuring an interpupillary distance of the observer,
- (b) determining a visual threshold of the observer's eyes,
- (c) presenting a sequence of first and second images on respective first and second sets of pixels of a pair of image arrays as a pair of dichoptic stimuli of substantially equal intensity greater than a predetermined visual threshold by a predetermined equalizing factor such that the two images may be moved relatively closer together or further apart by illuminating different pixels of at least one of said sets of pixels,
- (d) for each sequence of images presented, extinguishing and illuminating different pixels in at least one of said sets so as to move the two images relatively closer together or further apart until both images appear to the observer to be aligned,
- (e) measuring any actual displacement T between the two images, and
- (f) calculating a distance of dark vergence according to the formula:

$$D_c = \frac{P_d D_o}{P_d - f(T)}$$

where:
$D_c$ is the distance of dark vergence;

$P_d$ is the interpupillary distance;
$D_o$ is the distance of an optical pathway from the observer to a viewing plane of the image arrays; and
f(T) is a polynomial function of the measured displacement T between the pair of dichoptic stimuli which approximates the measured displacement T for at least a predetermined number of images at an end of said sequence.

12. The method according to claim 11 for determining the observer's dark vergence in a predetermined direction, wherein prior to performing step (c) there is further included the step of preventing the observer from seeing the dichoptic stimuli other than by looking in said predetermined direction.

13. The method according to claim 12, wherein the dichoptic stimuli are propagated to the eyes of the observer via an inclined reflecting element which is normal to the eyes when they are directed in said predetermined direction, and the step of preventing includes disposing an optically opaque element in front of the eyes of the observer so as to prevent straight-ahead vision.

14. The method according to claim 11, wherein step (b) comprises:
- (a) dark adapting the observer,
- (b) presenting two simultaneous stimuli on the respective sets of pixels at a predetermined nominal threshold intensity so as to be seen by respective eyes of the observer, and
- (c) lowering the intensity of the respective stimuli in stepwise manner until the respective stimuli are only just perceptible to the observer.

15. A method for determining a dark vergence of an observer in a predetermined direction, comprising the steps of:
- (a) determining a relationship $K=f(\theta)$ between eye position $\theta$ and a measurable physical variable K using a conventional eye position measuring means,
- (b) dark adapting the observer,
- (c) directing a visual stimulus towards the observer so as to cause the observer's eyes to gaze at a new eye position in said predetermined direction at a new dark vergence angular position $\theta_c$, said visual stimulus being of sufficiently short duration to prevent convergence of the observer's eyes and thus to appear as a dichoptic stimulus,
- (d) measuring the physical variable K at the new eye position with said conventional eye position measuring means and thus determining from said relationship $K=f(\theta)$ the observer's dark vergence in the predetermined direction being equal to the new angular position $\theta_c$ of the observer's eyes.

16. The method according to claim 15, wherein:
the visual stimulus is a sequence of N flashes occurring every 2 to 5 seconds and each having a duration less than 100 ms,
after each flash a mean eye position $P_i$ is measured, and the dark vergence $\theta_c$ is calculated in accordance with the formula:

$$\theta_c = \frac{K}{n}\sum_{n=1}^{N} P_i.$$

17. An apparatus for presenting two simultaneous images on respective sets of pixels as a dichoptic stimulus of substantially equal intensity, the apparatus comprising:

a first control means coupled to the first set of pixels for illuminating a predetermined number $N_1$ of said pixels so as to present a first image to a first eye of an observer at a predetermined intensity, and a second control means coupled to the second set of pixels for illuminating a predetermined number $N_2$ of said pixels so as to display a second image to a second eye of the observer at an intensity equal to said predetermined intensity multiplied by a predetermined equalization factor equal to $$\frac{lgA_2}{lgA_1}.$$

18. The apparatus according to claim 17, further including:
    third control means operable by the observer for indicating an apparent displacement between the two images so as to produce a corresponding signal;
    the second control means being coupled to the third control means and being responsive to said signal for illuminating different ones of said pixels so as effectively to move the second image relative to the first image in a direction to correct said apparent misalignment.

19. The apparatus according to claim 18, wherein the video display unit is a display monitor of a computer, and there is further included:
    a telescopic tunnel disposed between the video display unit and the observer and having a non-reflecting inner surface, the telescopic tunnel permitting variation of a distance between the observer and the video display unit,
    an obstruction means for preventing the observer from viewing directly towards the video display unit, and
    a reflection means inclined at a predetermined angle for reflecting the first and second images towards the respective eyes of the observer.

20. The apparatus according to claim 18, wherein the first and second images may be moved relatively closer together or further apart and the third control means includes "toward" and "apart" indication means for indicating the corresponding misalignment between the first and second images.

21. The apparatus according to claim 20, wherein the first and second sets of pixels are associated with respective LCDs.

22. The apparatus according to claim 21, further including first and second reflecting elements for reflecting the respective first and second images to the respective eyes of the observer so as to be seen by the observer as respective first and second virtual images at a distance $D_o$ from the observer.

23. The apparatus according to claim 22, wherein the first and second reflecting elements are built into respective eyepieces of a pair of spectacles worn by the observer.

24. The apparatus according to claim 23, wherein the respective eyepieces of the spectacles further include an obstruction means for preventing straight-ahead vision.

25. The apparatus according to claim 17, wherein the first and second control means are responsively coupled to the third control means for producing said successive images a predetermined time interval after operation of the second control means.

26. The apparatus according to claim 25, further including randomizing means coupled to the third control means and responsive to an elapsed time between display of a respective pair of images and the production of said corresponding signal by the third control means for determining said predetermined time interval as a random function of said elapsed time.

27. The apparatus to claim 17, further including computing means responsive to an actual displacement between the first and second images when they appear aligned to the observer for computing a distance of dark vergence of the observer according to the formula:

$$D_c = \frac{P_d D_o}{P_d - f(T)}$$

where:
    $D_c$ is the distance of dark vergence;
    $P_d$ is an interpupillary distance;
    $D_o$ is a distance from the observer to a viewing plane of the video display unit; and
    f(T) is a polynomial function of a measured displacement T between the two dichoptic images which approximates the measured displacement T for at least a predetermined number of images at an end of said sequence.

28. An apparatus for determining a dark vergence $\theta_c$ of an observer in a predetermined direction, comprising:
    (a) a conventional eye position measuring means having a known relationship $K=f(\theta)$ between eye position $\theta$ and a measurable physical variable K, and
    (b) directing means for directing a visual stimulus towards the observer so as to cause the observer's eyes to move to said desired angular position $\theta_c$ and gaze at a new eye position in said predetermined direction, said visual stimulus being of sufficiently short duration to prevent convergence of the observer's eyes and thus to appear as a dichoptic stimulus;
    whereby measuring the physical variable K at the new eye position with said conventional eye position measuring means permits determination from said relationship $K=f(\theta)$ of the observer's dark vergence in the predetermined direction being equal to the new angular position $\theta_c$ of the observer's eyes.

29. The apparatus according to claim 28, wherein:
    the visual stimulus is a sequence of N flashes every 2 to 5 seconds and each having a duration less than 100 ms, after each flash a mean eye position $P_i$ is measured, and the dark vergence $\theta_c$ is calculated in accordance with the formula:

$$\theta_c = \frac{K}{n}\sum_{n=1}^{N} P_i.$$

* * * * *